US005756689A

United States Patent [19]

Busman et al.

[11] Patent Number: 5,756,689
[45] Date of Patent: May 26, 1998

[54] DIAZO COMPOUNDS FOR LASER-INDUCED MASS TRANSFER IMAGING MATERIALS

[75] Inventors: Stanley C. Busman, Minneapolis; Gregory D. Cuny, Woodbury; Krzysztof A. Zaklika, St. Paul, all of Minn.; Richard J. Ellis, Great Dunmow, United Kingdom

[73] Assignee: Minnesota Mining and Manufacturing Company, St. Paul, Minn.

[21] Appl. No.: 858,307

[22] Filed: May 19, 1997

Related U.S. Application Data

[63] Continuation of Ser. No. 627,160, Apr. 3, 1996, Pat. No. 5,691,098.

[51] Int. Cl.⁶ .................................................. C07C 245/00
[52] U.S. Cl. ............................ 534/560; 534/558; 534/561
[58] Field of Search ................................ 534/558, 560, 534/561

[56] References Cited

U.S. PATENT DOCUMENTS

| | | |
|---|---|---|
| 4,038,253 | 7/1977 | Kramer. |
| 4,039,521 | 8/1977 | Smith. |
| 4,339,522 | 7/1982 | Balanson et al. ............ 430/192 |
| 4,491,432 | 1/1985 | Aviram et al.. |
| 4,559,824 | 12/1985 | Sachdev et al.. |
| 5,089,372 | 2/1992 | Kirihata et al. ............ 430/167 |
| 5,156,938 | 10/1992 | Foley et al. ................. 430/200 |
| 5,171,650 | 12/1992 | Ellis et al. ................... 430/20 |
| 5,198,322 | 3/1993 | Wilharm et al. ............ 430/189 |
| 5,278,023 | 1/1994 | Bills et al. .................. 430/201 |
| 5,308,737 | 5/1994 | Bills et al. .................. 430/201 |
| 5,326,826 | 7/1994 | Rosechert et al. .......... 430/192 |

FOREIGN PATENT DOCUMENTS

| | | |
|---|---|---|
| 63-161445 | 7/1988 | Japan. |
| 1 470 530 | 4/1977 | United Kingdom. |

OTHER PUBLICATIONS

Photopolymerization of Surface Coatings—Jun. 1982, John Wiley and Sons, Interscience publication.
Diazo Compounds, Properties & Synthesis, Academic Press, New York 1986.
Indian Journal of Chemistry, vol. 25B, Jul. 1986, pp. 735–737.
IEEE Transactions on Electron Devices, vol. Ed. 28, No. 11, Nov. 1981.
J. Org. Chem., vol. 42, No. 17, 1997.
Angew. Chem. Int. Ed./vol. 6 (1967) No. 9.
Liebigs Ann. Chem., 676, 101–109 (1964).
Chem. Ber. 102, 1743–1754 (1969).
B. Eistert, D. Greiber Und I. Caspari, 1962 pp. 64–81.
JACS, 49, 1280 (1927).

*Primary Examiner*—Christopher G. Young
*Attorney, Agent, or Firm*—Arlene K. Musser; H. Sanders Gwin

[57] ABSTRACT

The invention relates to a method of increasing the sensitivity of laser induced thermal imaging by using certain diazo compounds. The diazo compounds contain functional groups adjacent the diazo substituent capable of stabilizing these compounds. The invention is useful in the field of thermal transfer imaging for the production of various graphic arts media.

2 Claims, No Drawings

DIAZO COMPOUNDS FOR LASER-INDUCED MASS TRANSFER IMAGING MATERIALS

This is a continuation of application Ser. No. 08/627160 filed Apr. 03, 1996 U.S. Pat. No. 5,691,098.

FIELD OF THE INVENTION

This invention relates to the field of thermally imageable materials, specifically for laser induced thermal imaging. In particular, this invention pertains to the method of improving sensitivity in laser induced thermal imaging using diazo compounds. The method is useful in the production of color proofs, printing plates, films, printed circuit boards, and other graphic arts media that use thermal transfer imaging methods.

BACKGROUND OF THE INVENTION

Laser induced thermal imaging has long been used in the production of printing plates, image setting films, and proofing materials that require only dry processing. One type of laser imaging involves thermal transfer of material from donor to receptor. This is a complex non-equilibrium process, believed to involve both softening and thermal degradation of the material undergoing transfer, as discussed in Tolbert, W. A. et al., *J. Imaging Sci. Technol.*, 37, 411 (1993). Thermal degradation leads to gas production, and expansion of the gas may propel the remaining material to a receptor (ablation) or cause delamination from the donor substrate. Softening of the material permits adhesion of the material to the receptor. Thus the process may involve an ablation mechanism, a melt-stick mechanism, or both in combination.

Specifically, infrared light which has been generated by a laser is first absorbed by a radiation absorber (e.g., an infrared absorbing material such as an infrared dye, black alumina, or carbon black) and then converted to heat to decompose the energetic compound. As used herein, an "energetic compound" is a compound (e.g., a polymer) that exothermically decomposes to generate gases, shock waves, pressure, etc., when heated above a certain threshold temperature on the millisecond to nanosecond timescale. Examples of such energetic compounds include diazonium salts as well as compounds containing azo, azido, nitrato, and nitramino groups, such as nitrocellulose, polyvinyl nitrates, and the like.

Typically, in laser induced ablation-transfer imaging, heating rates elf 1 billion° C./second and pressures greater than 100 atmospheres (10 MPa) can occur. Although superheating of the radiation absorber can cause temperatures to reach 600° C., the threshold for ablation of a donor layer comprising a thermal mass transfer material might not be reached during the very short time period of this heating process. As a result, materials that have a lower threshold to ablation have been used in order to increase the sensitivity of the donor layer. Azide containing polymers, such as glycidyl azide polymers (GAP) and poly[bis(azidomethyl)] oxetane (BAMO), which are disclosed U.S. Pat. Nos. 5,278,023 (Bills et al.) and 5,308,737 (Bills et al.), have been utilized in lowering the thresh of ablation.

Although these are useful materials, they have limited applicability because they are incompatible with a number of infrared dyes such that dye lifetime stability is poor. Thus, a need exists for other compounds that will lower the threshold of ablation, increase sensitivity, and are useable with a wide variety of infrared dyes.

SUMMARY OF THE INVENTION

In accordance with the present invention, the sensitivity of laser induced thermal imaging systems can be increased by using diazo compounds that contain at least one electron withdrawing functional group adjacent the diazo substituent capable of stabilizing the diazo substituent (i.e., the $=N^+=N^-$ substituent). Preferably, at least two such functional groups are present in the compound.

One embodiment of the invention is a thermal transfer donor element comprising a substrate having coated on at least a portion thereof, in one or more layers: (a) a compound having a diazo substituent and at least one electron withdrawing functional group adjacent the diazo substituent; (b) a nondiazo radiation absorber; and (c) a thermal mass transfer material; wherein the diazo compound has a decomposition temperature of no greater than about 250° C.

Another embodiment of the present invention is a thermal transfer system comprising the thermal transfer donor element listed above and an image-receiving element. This can be used in a process for forming an image comprising the steps of: (a) bringing the thermal transfer donor element into contact with an image-receiving element; and (b) imagewise exposing the construction of (a), thereby transferring the thermal mass transfer material of the thermal transfer donor element to the image-receiving element.

The diazo compound used in the thermal transfer donor element preferably has the formula:

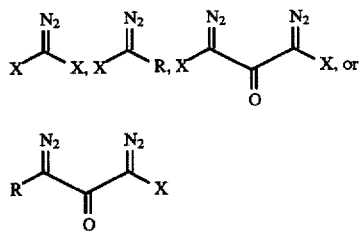

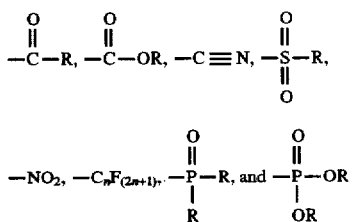

wherein each X is independently selected from the group consisting of:

$$-\overset{O}{\underset{\|}{C}}-R,\ -\overset{O}{\underset{\|}{C}}-OR,\ -C\equiv N,\ -\overset{O}{\underset{\underset{O}{\|}}{\overset{\|}{S}}}-R,$$

$$-NO_2,\ -C_nF_{(2n+1)},\ -\overset{O}{\underset{\underset{R}{|}}{\overset{\|}{P}}}-R,\text{ and }-\overset{O}{\underset{\underset{OR}{|}}{\overset{\|}{P}}}-OR$$

wherein each R is independently H or an organic group.

As used herein, the term "organic group" means a hydrocarbon group that is classified as an aliphatic group, cyclic group, or combination of aliphatic and cyclic groups (e.g., aralkyl and alkaryl groups). The term "aliphatic group" means a saturated or unsaturated, linear or branched hydrocarbon group. This term includes alkyl, alkoxy, alkenyl, vinyl, and alkynyl groups. The term "alkenyl group" means an unsaturated, linear or branched hydrocarbon group with one or more double bonds. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. This term includes cycloalkyl, cycloalkenyl, and cycloalkynyl groups. The term "aromatic group" or "aryl group" means a mono- or polynuclear aromatic hydrocarbon group. The term "heterocyclic group" means a closed ring hydrocarbon in which one or more of the atoms in the ring is an element other than carbon (e.g., sulfur, nitrogen, oxygen, etc.).

As is well understood in this technical area, a large degree of substitution is not only tolerated, but is often advisable. Substitution is anticipated in the compounds of the present invention. As a means of simplifying the discussion and recitation of certain terminology used throughout this application, the terms "group" and "moiety" are used to differentiate between chemical species that allow for substitution or that may be substituted and those that do not so allow or may not be so substituted. Thus, when the term "group" is used to describe a chemical substituent, the described chemical material includes the unsubstituted group and that group with nonperoxidic O, N, or S atoms, for example, in the chain as well as carbonyl groups or other conventional substitution. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, t-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, sulfoalkyls, etc. On the other hand, the phrase "alkyl moiety" is limited to the inclusion of only pure open chain saturated hydrocarbon alkyl substituents, such as methyl, ethyl, propyl, t-butyl, and the like.

DETAILED DESCRIPTION OF THE INVENTION

Laser-addressable thermal transfer materials for producing color proofs, printing plates, films, printed circuit boards, and other media are provided. The materials contain a substrate on which is coated a light-to-heat converting (LTHC) composition. The element includes a layer containing a material capable of producing nitrogen ($N_2$) gas (i.e., the "energetic compound"). This material is a diazo compound ($R=N^+=N^-$). Within this layer, or in a separate layer or layers, is a nondiazo radiation absorber and a thermal mass transfer material. The thermal mass transfer material, which can contain, for example, pigments, toner particles, resins, metal particles, monomers, polymers, dyes, or combinations thereof, can be incorporated into the layer containing the diazo compound or into an additional layer or layers coated onto the layer containing the diazo compound. The nondiazo radiation absorber can be employed in one of these layers or in a separate layer to achieve localized heating with an electromagnetic energy source, such as a laser, which induces the rapid expansion of gas and causes the thermal mass transfer material to be propelled to the receptor, for example.

Diazo Compounds

Diazo compounds that are suitable for use in the thermal transfer materials (e.g., thermal transfer donor element) of the present invention are those compounds containing a diazo substituent and at least one electron withdrawing functional group adjacent to the diazo substituent. Preferably, at least two such electron-withdrawing functional groups are present in the compound. The electron withdrawing group is believed to be capable of stabilizing the diazo substituent. Although the inventors do not wish to be bound by theory, these stable diazo compounds are believed to increase the laser thermal transfer efficiency of a construction by lowering its vaporization and/or decomposition temperature.

Electron withdrawing groups have a positive Hammett sigma value. Preferably, the electron withdrawing groups have a Hammett sigma value of greater than about 0.1, and more preferably greater than about 0.4. "Hammett sigma value" is equivalent to the Hammett $\sigma_p$ constant as defined by the Hammett equation:

$$\log K/K° = \sigma_p \rho$$

wherein K° is the acid dissociation constant of the unsubstituted benzoic acid in aqueous solution at 25° C., K is the corresponding constant for the para-substituted acid, and ρ is the reaction parameter, which is defined as 1.0 for the dissociation of para-substituted benzoic acids. Examples of functional groups with a positive Hammett sigma value include, but are not limited to, carbonyl groups (e.g., formyl groups, keto groups, etc.), oxycarbonyl groups (e.g., carboxylic ester groups, carboxylic acid groups), sulfonyl groups (e.g., alkylsulfonyl groups, etc.), cyano groups (i.e., nitrile groups), nitro groups, perfluoroalkyl groups (e.g., trifluoromethyl, perfluorooctyl, etc.), phosphine oxide groups (e.g., phosphonate and phosphinate groups), as well as other groups described in Lange's *Handbook of Chemistry*, 14th edition, McGraw-Hill, Chapter 9, pp 2–7 (1992).

For efficient thermal transfer, suitable diazo compounds possess a decomposition temperature of no greater than about 250° C., preferably no greater than about 200° C., more preferably no greater than about 180° C., and most preferably no greater than about 170° C. The decomposition temperature is defined by the peak of the exotherm or endotherm measured by Differential Scanning Calorimetry in a closed pan at a heating rate of 10° C. per minute. Higher decomposition temperatures can generally be tolerated if the diazo compounds vaporize, e.g., sublime, at a relatively low temperature. Preferably, suitable diazo compounds vaporize at a temperature of less than about 150° C., and more preferably less than about 130° C. The vaporization temperature is that temperature at which a 5% weight loss is measured by thermal gravimetric analysis at a heating rate of 10° C. per minute under nitrogen flow of 50 ml/minute (at standard temperature and pressure, i.e., 25° C. and 1 atmosphere).

It is particularly desirable for the diazo compounds to possess a low decomposition temperature and a low vaporization temperature. For adequate shelf stability and handleability, however, preferably, the diazo compounds possess a decomposition temperature of at least about 110° C. and/or vaporize at a temperature of at least about 60° C. More preferably, the diazo compounds have a decomposition temperature of at least about 120° C. and/or vaporize at a temperature of at least about 80° C. Most preferably, the diazo compounds have a decomposition temperature of at least about 130° C. and/or vaporize at a temperature of at least about 90° C.

A class of diazo compounds useful in this invention have the following formulae:

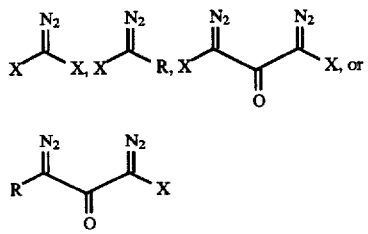

wherein each X is independently selected from the group consisting of:

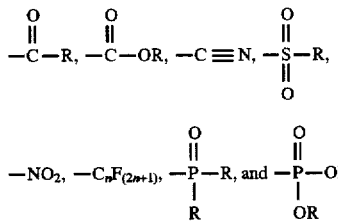

Preferably, each X is independently selected from the group consisting of —C(O)R, —C(O)OR, and —CN. More preferably, each X is a —C(O)R group or a —C(O)OR group. Most preferably, each X is a —C(O)R group.

In the above formulae, each R is independently H or an organic group, i.e., an aliphatic group, cyclic group, or combination of aliphatic and cyclic groups (e.g., aralkyl and alkaryl groups), including saturated or unsaturated, linear or branched hydrocarbon groups, and closed ring hydrocarbon groups (e.g., alicyclic groups, aromatic groups, or heterocyclic groups, all of which can include one or more rings). The compound can be monomeric, oligomeric, or polymeric. For monomeric compounds, R is an organic group having less than about 30 carbon atoms. Furthermore, the two R groups, when taken together with the remainder of the molecule, can form a compound having one or more rings, typically, five, six, or seven membered rings.

Preferably, R is a ($C_1$–$C_{30}$)aliphatic group, a ($C_7$–$C_{30}$) alkaryl group, a ($C_7$–$C_{30}$)aralkyl group, a ($C_6$–$C_{30}$)aryl group, a ($C_5$–$C_{30}$)heterocyclic group. In any one molecule these two R groups may or may not be joined to form one or more rings. More preferably, R is a ($C_1$–$C_{15}$)alkyl group, a ($C_7$–$C_{15}$)alkaryl group, a ($C_7$–$C_{15}$) aralkyl group, a ($C_6$–$C_{15}$)aryl group, or a ($C_5$–$C_{15}$)heterocyclic group. Most preferably, R is a ($C_1$–$C_5$)alkyl moiety, two of which can be joined to form a ring. Preferably, n=1–18.

Examples of the above compounds include 5-diazo-2,2-dimethyl-4,6-dioxo-1,3-dioxane (Compound I, often referred to as "Meldrum's Diazo"), 5-diazo-4,6-dioxo-2-methyl-2-(2-phenethyl)-1,3-dioxane (Compound II, often referred to as Benzyl Acetone Meldrum's Diazo), diethyl 2-diazomalonate (Compound III), 2-diazo-3-oxobutyroxyethyl methacrylate (Compound V), poly(2-diazo-3-oxobutyroxyethyl methacrylate) (Compound IV), dimedone diazo (Compound VI), 2-diazo-1-phenyl-1,3-butanedione (Compound VII), di-t-butyl-2-diazomalonate (Compound VIII), di-t-butyl-2,4-diazo-3-oxo-glutarate (Compound IX, often referred to as "Bis Diazo"), ethyl-2-diazo-3-oxo-3-phenylpropanate (Compound X), 3-diazo-1,8,8-trimethylbicyclo[3.2.1]octan-2,4-dione (Compound XI, often referred to as methylene camphoroquinone diazo), (diazobenzyl)diphenylphosphine oxide, 2-diazo-1,2-diphenyl-1-ethanone, (diazophenacyl)diphenylphosphine oxide, 2-diazo-1,3-diphenyl-1,3-propanedione, methyl diazo(diphenylphosphoryl)acetate, methyl 2-diazo-3-oxo-3-phenylbutyrate, ethyl diazo(diethoxyphosphoryl)acetate, diethyl (diazobenzyl)phosphonate, and ethyl diazophenylacetate.

For certain embodiments of the present invention, particularly preferred diazo compounds have the following formulae:

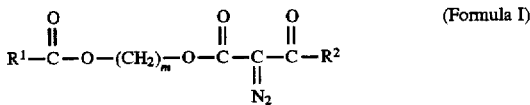

wherein $R^1$ is H or a ($C_1$–$C_4$)aliphatic group, preferably a ($C_2$–$C_4$)alkenyl group; $R^2$ is as described above for R; and m=2–10.

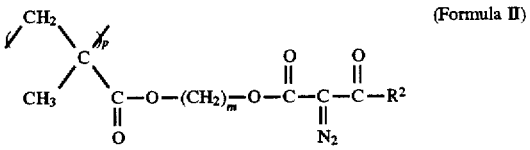

wherein p=2–1000; $R^2$ and m are as defined above; and

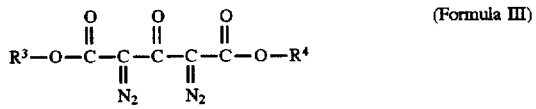

wherein $R^3$ and $R^4$ are independently selected from the group consisting of a ($C_1$–$C_{15}$)alkyl group, a ($C_7$–$C_{15}$) alkaryl group, a ($C_7$–$C_{15}$)aralkyl group, a ($C_6$–$C_{15}$)aryl group, and a ($C_5$–$C_{15}$)heterocyclic group. A specific example of Formula I is 2-diazo-3-oxobutyroxyethyl methaciylate (Compound V). A specific example of Formula II is poly(2-diazo-3-oxobutyroxyethyl methacrylate) (Compound IV). A specific example of Formula III is di-t-butyl-2,4-diazo-3-oxo-glutarate (Compound IX).

Thermal Mass Transfer Materials

Thermal mass transfer materials are materials that can be removed from a substrate or donor element by the process of absorption of intense electromagnetic radiation. Depending on the intensity of the light, light to heat conversion within or adjacent the materials can cause a melting of materials and/or gas production within or adjacent to them. Gas production may be the result of evaporation, sublimation, or thermal decomposition to gaseous products. Expansion of the gas may cause delamination from the donor substrate or propulsion of materials from the donor to a receptor. The latter process is often termed ablation. Melting or softening of the material promotes adhesion to the receptor. The overall transfer process thus involves ablative or melt-stick transfer or a combination of the two.

Thermal mass transfer materials suitable for use in the present invention are materials that can undergo a light-induced thermal mass transfer from the thermal transfer donor element. Typically, these are materials that can be transferred to an image-receiving element in an imagewise fashion. Depending on the desired application, the thermal mass transfer material can include one or more of the following: dyes; metal particles or films; selective light absorbers such as infrared absorbers and fluorescing agents for identification, security and marking purposes; pigments; semiconductors; electrographic or electrophotographic toners; phosphors such as those used for television or medical imaging purposes; electroless plating catalysts; polymerization catalysts; curing agents; and photoinitiators.

For color transfer printing a dye is typically included in the thermal mass transfer material. Suitable dyes include those listed in Venkataraman, *The Chemistry of Synthetic Dyes*; Academic Press, 1970: Vols. 1–4 and *The Colour Index Society of Dyers and Colourists*, Yorkshire, England, Vols. 1–8. Examples of suitable dyes include cyanine dyes (e.g., streptocyanine, merocyanine, and carbocyanine dyes), squarylium dyes, oxonol dyes, anthraquinone dyes, diradical dicationic dyes (i.g., IR165), and holopolar dyes, polycyclic aromatic hydrocarbon dyes, etc. Similarly, pigments can be included within the thermal mass transfer material to impart color and/or fluorescence. Examples are those known for use in the imaging arts including those listed in the *Pigment Handbook*; Lewis, P. A., Ed.; Wiley, N.Y. 1988, or available from commercial sources such as Hilton-Davis, Sun Chemical Co., Aldrich Chemical Co., Imperial Chemical Industries, etc.

For applications such as preparation of printed circuits, encapsulation of electronic components and the like, it may be desirable to incorporate materials such as metal or metal oxide particles, fibers or films within the thermal mass transfer material. Suitable metal oxides include titanium dioxide, silica, alumina, and oxides of chromium, iron, cobalt, manganese, nickel, copper, zinc, indium, tin, antimony and lead, and black alumina. Suitable metal films or particles can be derived from atmospherically stable metals including, but not limited to, aluminum, scandium, titanium, vanadium, chromium, manganese, iron, cobalt, nickel, copper, zinc, gallium, germanium, yttrium, zirconium, niobium, molybdenum, ruthenium, rhodium, palladium, silver, cadmium, indium, tin, antimony, lanthanum, gadolinium, hafnium, tantalum, tungsten, rhenium, osmium, iridium, platinum, gold, thallium, and lead. Alternatively, semiconductors can be included within the thermal mass transfer material. Suitable semiconductors include carbon (including diamond and graphite), silicon, arsenic, gallium arsenide, gallium antimonide, gallium phosphide, aluminum antimonide, indium tin oxide, zinc antimonide, etc.

It is often desirable to transfer thermal mass transfer materials to a substrate to provide a modified surface (for example, to increase or decrease adhesion or wetability) in an imagewise fashion. For those applications, the transfer materials can include polymers or copolymers such as silicone polymers as described by M. W. Ranney in *Silicones*; Noyes Data Corp., 1977, Vols. 1 and 2. Other such materials that can be used include fluorinated polymers, polyurethanes, acrylic polymers, epoxy polymers, polyolefins, styrene-butadiene copolymers, styrene-acrylonitrile copolymers, polyetliers, polyesters, acetals or ketals of polyvinyl alcohol, vinyl acetate copolymers, vinyl chloride copolymers, vinylidine chloride copolymers, cellulosic polymers, condensation polymers of diazonium salts, and phenolic resins such as novolac resins and resole resins.

In other applications it is desirable to transfer curable materials such as monomers or uncured oligomers or crosslinkable resins. In those applications the thermal mass transfer material may be a polymerizable monomer or oligomer. The properties of the material should be selected so that volatility of the monomer or oligomer is minimal to avoid storage problems. Suitable polymerizable materials include acrylate- or epoxy-terminated polysiloxanes, polyurethanes, polyethers, epoxides, etc. Suitable thermal crosslinkable resins include isocyanates, melamine formaldehyde resins, etc. Polyinerizable and/or crosslinkable, transferrable binders are particularly valuable for the manufacture of filter arrays for liquid crystal devices, in which the color layer must resist several subsequent aggressive treatment steps.

If the thermal mass transfer elements of the present invention are multilayer constructions, the thermal mass transfer material is in the outermost layer(s). Thus, not only is a one-layer construction possible that includes the thermal mass transfer material, the nondiazo radiation absorber, and the diazo compound, but each of these materials could be in a separate layer. Alternatively, any two of them could be combined in one layer and the third in a second layer. For example, the topcoat could include the thermal mass transfer material (e.g., a toner or pigment in an organic polymeric binder, in one or more layers) and an underlying layer could include the diazo compound and the nondiazo radiation absorber. Thus, whether one or more layers are used, the only requirement is that the thermal mass transfer material be in the outermost layer or layers.

Nondiazo Radiation Absorbers

The nondiazo radiation absorber (i.e., a radiation absorber that does not include a diazo compound) is one that can be used to absorb radiation emitted from a high intensity, short duration, light source such as a laser. It serves to sensitize the thermal transfer donor element to various wavelengths of radiation, and to convert incident electromagnetic radiation into thermal energy. That is, the radiation absorber acts as a light-to-heat conversion element. It is generally desirable for the radiation absorber to be highly absorptive of the incident radiation so that a minimum amount (weight percent for soluble absorbers or volume percent for insoluble absorbers) can be used in coatings. Typically, the nondiazo radiation absorber is a black body absorber or an organic pigment or dye that provides an optical density of about 0.2–3.0.

The amount of LTHC used in the construction will be chosen depending on efficiency of conversion of light into heat, the absorptivity of the LTHC at the exposure wavelength, and thickness or optical path length of the construction. It is preferred that no more than about 50% by weight of the LTHC be used, except when the LTHC is present in a separate layer, in which case amounts up to 100% may be used. A broad range of LTHCs can be employed and some nonlimiting examples follow.

Dyes are suited for this purpose and may be present in particulate form or preferably substantially in molecular dispersion. Especially preferred are dyes absorbing in the IR region of the spectrum. Examples of such LTHC dyes may be found in Matsuoka, M., *Infrared Absorbing Materials*, Plenum Press, New York, 1990, in Matsuoka, M., *Absorption Spectra of Dyes for Diode Lasers*, Bunshin Publishing Co., Tokyo, 1990, in U.S. Pat. Nos. 4,833,124 (Lum), 4,912,083 (Chapman et al.), 4,942,141 (DeBoer et al.), 4,948,776 (Evans et al.), 4,948,777 (Evans et al.), 4,948,778 (DeBoer), 4,950,639 (DeBoer), 4,952,552 (Chapman et al.), 5,023,229 (Evans et al.), 5,024,990 (Chapman et al.), 5,286, 604 (Simmons), 5,340,699 (Haley et al.), 5,401,607 (Takiff et al.) and in European Patent No. 568,993 (Yamaoka et al.). Additional dyes are described in Bello, K. A. et al., *J. Chem. Soc. Chem. Commun.*, 452 (1993) and U.S. Pat. No. 5,360, 694 (Thien et al.). IR absorbers marketed by American Cyanamid or Glendale Protective Technologies, Inc., Lakeland, Fla., under the designation CYASORB IR-99, IR-126 and IR-165 may also be used, as disclosed in U.S. Pat. No. 5,156,938 (Foley et al.). Further examples of LTHCs may be found in U.S. Pat. Nos. 4,315,983 (Kawamura et al.), 4,415,621 (Specht et al.), 4,508,811 (Gravesteijn et al.), 4,582,776 (Matsui et al.), and 4,656,121 (Sato et al.). In addition to conventional dyes, U.S. Pat. No. 5,351,617 (Williams et al.) describes the use of IR-absorbing conductive polymers as LTHCs. As will be clear to those skilled in the art, not all the LTHC dyes described will be suitable for every construction. Such dyes will be chosen for solubility in, and compatibility with, the specific polymer, sublimable material, and coating solvent in question.

Pigmentary materials may also be dispersed in the construction as LTHCs. Examples include carbon black and graphite, disclosed in U.S. Pat. Nos. 4,245,003 (Oruanski et al.), 4,588,674 (Stewart et al.), 4,702,958 (Itoh et al.), and 4,711,834 (Butters et al.), and British Patent No. 2,176,018 (Ito et al.), as well as phthalocyanines, nickel dithiolenes, and other pigments described in U.S. Pat. Nos. 5,166,024 (Bugner et al.) and 5,351,617 (Williams et al.). Additionally, black azo pigments based on copper or chromium complexes of, for example, pyrazolone yellow, dianisidine red, and nickel azo yellow are useful. Inorganic pigments are also valuable. Examples are disclosed in U.S. Pat. Nos. 5,256,506 (Ellis et al.), 5,351,617 (Williams et al., and 5,360,781 (Leenders et al.), for example, and include oxides and sulfides of metals such as aluminum, bismuth, tin, indium, zinc, titanium, chromium, molybdenum, tungsten, cobalt, iridium, nickel, palladium, platinum, copper, silver, gold, zirconium, iron, lead or tellurium. Metal borides, carbides, nitrides, carbonitrides, bronze-structured oxides, and oxides structurally related to the bronze family (e.g. $WO_{2.9}$) are also of utility, as taught by U.S. Pat. No. 5,351,617 (Williams et al.).

When dispersed particulate LTHCs are used, it is preferred that the particle size be less than about 10 micrometers, and especially preferred that it be less than about 1 micrometer. Metals themselves may be employed, either in the form of particles, as described for instance in U.S. Pat. No. 4,252,671 (Smith), or as films coplanar and contiguous with the thermal mass transfer layer, as disclosed in U.S. Pat. No. 5,256,506 (Ellis et al.). Suitable metals include aluminum, bismuth, tin, indium, tellurium and zinc.

The thickness of such a coplanar LTHC layer will be selected using well-known principles of optics to provide a good compromise between the amount of IR radiation absorbed and the amount reflected. In the case of metallic films, partial oxidation of the film during deposition, sputtering or vapor coating, for example, can be helpful in increasing absorption and decreasing reflection. Semiconductors such as silicon, germanium or antimony are also of utility as LTHCs, as described, for example, in U.S. Pat. Nos. 2,992,121 (Francis et al.) and 5,351,617 (Williams et al.).

When the LTHC is used in a construction in which the color of the image is important, as in the case of a color proof for instance, attention should be paid to ensuring that the LTHC does not contribute undesirable background color to the image. This may be done by using as the LTHC a dyestuff, such as a squarylium dye, with a narrow absorption in the infrared and consequently little or no light absorption in the visible region. If background color is important, a larger range of LTHCs may be used when the LTHC is incorporated in a separate layer, typically between the substrate and the material to be transferred.

Preferably, the nondiazo radiation absorbers employed in the thermal transfer donor elements of the present invention absorb in the near-infrared or infrared region of the electromagnetic spectrum. In some instances, it may be desirable to employ absorbers that absorb in the visible region of the electromagnetic spectrum, however.

Optional Additives

To improve the sensitivity of the thermal mass transfer materials utilized in the present invention, one or more accelerators for diazo decomposition may be added to the layer that includes the diazo "energetic compound" or a layer adjacent thereto. Useful accelerators for diazo decomposition include those materials known in the art to reduce the decomposition temperature of diazo compounds, including, but not limited to, copper salts and acids. However, these accelerators should not significantly decrease the decomposition temperature such that shelf life problems in the thermal mass transfer donor result.

Sensitivity of the thermal mass transfer donor elements of the present invention may also be increased by incorporation of a surfactant (as described by M. R. Porter in *Handbook of Surfactants*, Blackie, Chapman and Hall; New York, 1991), preferably a fluorochemical surfactant, as taught by EP 602,893 (Patel et al.) The surfactant may be incorporated in any of the layers of the thermal transfer donor element. Preferably, it is incorporated in the thermal mass transfer material in the top layer of the donor element in order to reduce cohesion. Nonlimiting examples of fluorochemical surfactants include that available under the trade designation "FLUORAD" from Minnesota Mining and Manufacturing Company (St. Paul, Minn.).

The thermal mass transfer elements can also include additives that enhance its film-forming properties, transfer characteristics, etc. Such additives include coating aids, dispersing agents, plasticizers, slip agents, UV absorbers, light stabilizers, antistatic agents, emulsifiers, defoamers, viscosity-controlling agents, lubricants, optical brighteners, antioxidants, preservatives, and the like.

Any of the layers of the construction can also include an organic polymeric binder. Exemplary binders are listed above in the discussion of the thermal mass transfer materials. Other suitable binders include a wide variety of thermoplastic resins, thermosetting resins, waxes, and rubbers. They may be homopolymers and copolymers. Multiple materials may be present simultanteously as compatible blends, phase separated systems, interpenetrating networks, and the like. Typically, these binders should be soluble or dispersible in organic solvents to aid in processing. Nonlimiting examples of such binders include olefinic resins, acrylic resins, styrenic resins, vinyl resins (including vinyl acetate, vinyl chloride, and vinylidine chloride copolymers), polyamide resins, polyimide resins, polyester resins, olefin resins, allyl resins, urea resins, phenolic resins (such as novolac and resole resins), melamine resins, polycarbonate resins, polyketal resins, polyacetal resins polyether resins, polyphenylene oxide resins, polyphenylene sulfide resins, polysulfone resins, polyurethane resins, fluorine-containing resins, cellulosic resins, silicone resins, epoxy resins, ionomer resins, rosin derivatives, natural (animal, vegetable, and mineral) and synthetic waxes, natural and synthetic rubbers (e.g., isoprene rubber, styrene/butadiene rubber, butadiene rubber, acrylonitrile/butadiene rubber, butyl rubber, chloroprene rubber, acrylic rubber, chlorosulfonated polyethylene rubber, hydrin rubber, urethane rubber, etc). Water dispersable resins or polymeric latexes or emulsions may be used.

Thermal Transfer Donor Elements

The thermal transfer donor elements of the present invention include a substrate on which is coated at least one layer of material that includes a compound having a diazo substituent and at least one electron withdrawing functional group adjacent to the diazo substituent (i.e., the diazo compound). This layer can also include a nondiazo radiation absorber and a thermal mass transfer material. Alternatively, these materials could be in separate layers, as long as the thermal mass transfer material is in the outermost layer(s). Thus, not only is a one-layer construction possible that includes the thermal mass transfer material, the LTHC, and the diazo compound, but each of these materials could be in a separate layer.

Alternatively, any two of them could be combined in one layer and the third in a second layer. For example, the topcoat could include a toner or pigment in an organic polymeric binder as the thermal mass transfer material in one or more layers, and an underlying layer could include the diazo compound and the LTHC. Thus, whether one or more layers are used, the only requirement is that the thermal mass transfer material be in the outermost layer(s). The thermal mass transfer material may itself comprise one or two layers, and in the latter case both the component layers of the mass transfer layer are transferred during the imaging process. For example, if the thermal mass transfer material has as its outermost layer a coating of adhesive, adhesion of the transferred coating to the receptor is promoted. This can be valuable if brittle or refractory materials must be transferred, or if it is not practical to apply an adhesion-promoting coating to the receiver element. Alternatively, the outermost layer(s) of the thermal mass transfer materials may contain colorants or reactive resins, while the layer just beneath the thermal mass transfer material can be used to limit bleeding or diffusion of the diazo compound or the LTHC into the topmost layer, or to assist the release of the mass transfer layer from the donor during imaging.

Whether in one layer or separate layers, the diazo compound and the nondiazo radiation absorber are used in amounts effective to provide decomposition of the diazo compound and formation of gaseous product(s). The thermal transfer material is present in an amount effective to provide a suitable image, printing plate, color proof, resist, conductive element, etc. Preferably, the diazo compound is present in an amount of about 5–65% by weight of the total coating, the nondiazo radiation absorber is present in an amount of about 5–50% by weight of the total coating, and the thermal transfer material is present in an amount of about 5–75% by weight of the total coating.

The substrate or support to which the thermal mass transfer donor elements are applied may be rigid or flexible. The support can be reflective or non-reflective with respect either to the wavelength of imaging light (including the infrared) or to other wavelengths. The carrier for the donor may be opaque, transparent, or translucent. In the case of a transparent carrier, optical imaging may be either from the coating side or from the carrier side. Any natural or synthetic product capable of being formed into fabric, mat, sheet, foil, film or cylinder is suitable as a substrate. The substrate may thus be glass, ceramic, metal, metal oxide fibrous materials, paper, polymers, resins, coated paper or mixtures, layers or laminates of such materials. Suitable donor substrates include sheets and films such as those made of plastic; glass; polyethylene terephthalate; fluorene polyester polymer consisting essentially of repeating interpolymerized units derived from 9,9-bis(4-hydroxyphenyl)fluorene and isophthalic acid, terephthalic acid or mixtures thereof; polyethylene; polypropylene; polyvinyl chloride and copolymers thereof; hydrolyzed and unhydrolyzed cellulose acetate. Preferably the donor substrate is transparent to the desired imaging radiation. However, any film that has sufficient transparency at the imaging wavelength and sufficient mechanical stability can be used. Nontransparent substrates which can be used include filled and/or coated opaque polyesters, aluminum supports, such as used in printing plates, and silicon chips. Prior to coating the thermal mass transfer layer or layers onto the substrate, the substrate may optionally be primed or treated (e.g. with a corona) to promote adhesion of the coating. The thickness of the substrates can vary widely, depending on the desired application. The donor material can be provided as sheets or rolls. Either of these can be single colored uniformly within the article, and multiple articles of different colors are used to produce a multi-colored image. Alternately, the donor materials could contain areas of multiple colors, with a single sheet or roll being used to generate multi-colored images.

The thermal transfer donor elements may be prepared by introducing the components into suitable solvents (e.g., tetrahydrofuran (THF), methyl ethyl ketone (MEK), toluene, methanol, ethanol, n-propanol, isopropanol, water, acetone, that available under the trade designation DOWANOL from Dow Chemical, Midland, Mo., etc., and mixtures thereof); mixing the resulting solutions at, for example, room temperature (i.e., 25°–30° C.); coating the resulting mixture onto the substrate; and drying the resultant coating, preferably at moderately elevated temperatures (e.g., 80° C.) Suitable coating techniques including knife coating, roll coating, curtain coating, spin coating, extrusion die coating, gravure coating, etc., can be used for applying the materials to a substrate.

When the thermal mass transfer material is coated as a separate layer on the layer containing the diazo compound it may be coated by a variety of techniques including, but not limited to, coating from a solution or dispersion in an organic or aqueous solvent (e.g., bar coating, knife coating, slot coating, slide coating, etc.), vapor coating, sputtering, gravure coating, etc., as dictated by the requirements of the transfer material itself Preferably, the layer containing the diazo compound has a thickness of about 0.1 micrometer to about 10 micrometers, more preferably about 0.2 micrometer to about 5 micrometers. The thermal mass transfer material may optionally be highly colored and, when coated in a separate layer, this layer preferably has a thickness of about 0.1 micrometer to 10 micrometers, and more preferably about 0.3 micrometer to about 2 micrometers.

Imagine Process

The thermal transfer donor elements of the present invention are typically used in combination with an image-receiving element. Suitable image-receiving (i.e., thermal mass transfer-receiving) elements are well known to those skilled in the art. Nonlimiting examples of image-receiving elements which can be utilized in the present invention include anodized aluminum and other metals; transparent polyester films (e.g., PET); opaque filled and opaque coated plastic sheets; a variety of different types of paper (e.g., filled or unfilled, calendared, eta.); fabrics (e.g., leather); wood; cardboard; glass, including ITO-coated conductive glass; printed circuit board; semiconductros; and ceramics. The image-receiving element can be untreated or treated to assist in the transfer/removal process or to enhance the adhesion of the transferred material. The receptor layer may also be prelaminated to the donor as disclosed in U.S. Pat. No. 5,351,617 (Williams et al.). This may be useful when the image is formed on the donor itself, and the prelaminated receptor serves to contain and limit the spread of ablation debris. The image is, thus, created on the donor and the receptor is peeled and discarded.

When used with an image-receiving element in the practice of the present invention, the thermal transfer donor and receiving elements are brought into intimate contact with one another such that upon irradiation, the thermal mass transfer material is transferred from the donor element to the receiving element. For example, the donor and image-receiving elements can be held in intimate contact by vacuum techniques (e.g., vacuum hold-down), positive pressure by the adhesive properties of the image-receiving element itself, or by prelamination, and imagewise heating the thermal transfer donor element (although the receptor could also be heated in addition to, or instead of, the donor). After transfer of the thermal mass transfer material from the donor to the image-receiving element, an image is created on the image-receiving element and the donor element may be removed from the image-receiving element. Alternatively, the thermal transfer donor elements of the present invention can be used without an image-receiving element and simply ablated to provide an imaged article. In this case, a peelable topcoat may be used to contain the ablated debris.

Thus, the donor elements of the present invention can be used in transfer printing, particularly color transfer printing and color proofing. They can also be used in masking applications, in which the transferred image is an exposure mask for use in resists and other light sensitive materials in the graphic arts or printed circuit industry. For such applications, the thermal transfer material would include a material effective in blocking the light output from common exposure devices. Suitable such materials include curcumin, azo derivatives, oxadiazole derivatives, dicinnamalacetone derivatives, benzophenone derivatives, etc. Alternatively, the thermal transfer material could include a material capable of etching a surface, such as a copper surface, and thereby form an etch resist.

A donor including metal particles in an adhesive can be selectively transferred to a circuit board to act as a conductive adhesive in chip bonding. When smaller volume fractions of conductive particles, or alternatively semiconductive particles, in a binder are transferred, resistive circuit elements may be prepared.

The donor elements of the present invention can also be used in the manufacture of printing plates. Here, durability can be achieved by crosslinking the imaged material, for instance with a brief high-temperature bake. For example, the donor elements of the present invention can also be used in the manufacture of waterless or lithographic printing plates. For lithographic printing plates, the transfer of oleophilic thermal transfer material to hydrophilic receptor such as grained, anodized aluminum is used. Preferably the thermal transfer material is transferred in an uncrosslinked state to maximize the sensitivity and resolution. The resulting printing plate can then be used for printing on a lithographic printing press using ink and fountain solution. Frequently, in order to increase the durability of the thermal transfer material after transfer, and thereby give a longer run-length printing plate, the thermal transfer material may contain crosslinking agents that crosslink the thermal transfer material upon application of heat or irradiation (e.g., UV). Examples of crosslinking agents that can be cured by the action of heat are melamine formaldehyde resins, such as that available under the trade designation CYMEL 303 from American Cyanamid Co., Wayne, N.J., in the presence of phenolic resins. Examples of crosslinking agents that can be cured by UV light are multifunctional acrylates, such as that available under the trade designation SR-295 from Sartomer Co., Westchester, Pa. The thermal crosslinking can be enhanced by the presence of catalysts and curing agents such as acids. Likewise, photocrosslinking can be enhanced by the presence of photoinitiators, photocatalysts, and the like.

The donor elements of the present invention can also be used in the manufacture of color filters for liquid crystal display devices. An example of a suitable color donor element for making color filters would be a coating of dye or pigment in a binder on a substrate. A laser or other focused radiation source is used to induce the transfer of the color material in an imagewise manner, often to a matrix-bearing (e.g., a black matrix) receptor sheet. An imaging radiation absorbent material may be included within the dye/pigment layer. A separate imaging radiation layer may also be used, normally adjacent to the color containing donor layer. The colors of the donor layer may be selected as needed by the user from amongst the many available colors normally or specially used in filter elements, such as cyan, yellow, magenta, red, blue, green, white and other colors and tones of the spectrum as contemplated. The dyes or pigments are preferably transmissive of preselected specific wavelengths when transferred to the matrix bearing receptor layer.

Imaging of the thermal mass transfer media of this invention is accomplished by a light source of short duration. Short exposure minimizes heat loss by conduction, so improving thermal efficiency. Suitable light sources include flashlamps and lasers. It is advantageous to employ light sources which are relatively richer in infrared than ultraviolet wavelengths to minimize photochemical effects and maximize thermal efficiency. Therefore, when a laser is used it is preferred that it emit in the infrared or near infrared, especially from about 700 to 1200 nm. Suitable laser sources in this region include Nd:YAG, Nd:YLF and semiconductor lasers. The preferred lasers for use in this invention include high power (>100 mW) single mode laser diodes, fiber-coupled laser diodes, and diode-pumped solid state lasers (e.g. Nd:YAG, and Nd:YLF), and the most preferred lasers are diode-pumped solid state lasers.

The entire construction may be exposed at once, or by scanning, or with a pulsed source, or at successive times in arbitrary areas. Simultaneous multiple exposure devices may be used, including those in which the light energy is distributed using optic fibers. Single-mode laser diodes, fiber-coupled laser arrays, laser diode bars, and diode-pumped lasers producing 0.1–12 W in the near infrared region of the electromagnetic spectrum may be employed for exposure. Preferably, a solid state infrared laser or laser diode array is used. Sources of relatively low intensity are also useful, provided they are focused onto a relatively small area.

Exposure may be directed at the surface of the imaging construction containing diazo compounds, or through a transparent substrate beneath such a donor construction, or through the transparent substrate of a receiving layer substantially in contact with the donor construction. Whatever the method of thermally imaging the materials of this invention, it is evident that they may be integrally or locally preheated below the imaging temperature prior to or during imaging.

Exposure energies will depend on the type of transfer employed, for example on whether the image is formed directly by removing material from the construction or by transfer to a receptor element. When a receptor element is used, the exposure may depend on the degree of contact with the donor, the temperature, roughness, surface energy and the like of the receptor. The rate of scanning during the exposure may also play a role, as may the thermal mass of the donor or receptor. Exposure energies will be chosen to provide a degree of transfer and a transfer uniformity sufficiently great to be useful. Laser exposure dwell times are preferably about 0.05–50 microseconds and laser fluences are preferably about 0.01–1 $J/cm^2$. Though imaged with light sources, the materials of this invention are not essentially photosensitive to visible light. The thermal nature of the imaging process typically allows the imaging constructions to be handled under normal room lighting.

The invention will be further described by reference to the following detailed examples. These examples are offered to further illustrate the various specific and preferred embodiments and techniques. It should be understood, however, that many variations and modifications may be made while remaining within the scope of the present invention.

EXAMPLE

Instrumentation

Thermographic Analysis (TGA) and Differential Scanning Calorimetry (DSC) measurements of materials were made using a DuPont Instruments 912 Differential Scanning Calorimeter and a 951 Thermogravimetric Analyzer. The TGA measurements were made using a heating rate of 10° C./minute under nitrogen flowing at a rate of 50 ml/minute (at standard temperature and pressure) and measured the weight loss from the sample during heating. The DSC measurements were made at a heating rate of 10° C./minute in sealed stainless steel pans which could withstand several atmospheres of pressure without leaking. This procedure was particularly important in testing compounds which exothermically decomposed with generation of gases. This procedure also prevented vaporization of compounds before their decomposition temperatures were reached. The DSC was used to measure the exothermicity (or endothericity) of decomposition in terms of Joules/gram and the decomposition temperature at the peak of the exotherm (or endotherm). Sample sizes were 2–5 mg for TGA and 1–5 mg for DSC. These results are summarized in the Table 1 below.

Three types of laser scanners were used: an internal drum type scanner suitable for imaging flexible substrates with a single beam Nd:YAG lasers; a flat field system suitable for imaging both flexible and rigid substrates with a single beam Nd:YAG laser; and an external drum system suitable for imaging flexible substrates with a fiber-coupled laser diode array.

For the internal drum system, imaging was performed using a Nd:YAG laser, operating at 1.064 micrometers in $TEM_{00}$ mode and focused to a 26 micrometer spot ($1/e^2$) with 3.2 watts of incident radiation at the image plane. The laser scan rate was 160 meters/second. Image data was transferred from a mass-memory system and supplied to an acousto-optic modulator which performed the image-wise modulation of the laser. The image plane consisted of a 135° wrap drum which was translated synchronously perpendicular to the laser scan direction. The substrate (donor and receptor) was firmly attached to the drum during the imaging using a vacuum hold-down. The donor and the receptor were translated in a direction perpendicular to the laser scan at a constant velocity, using a precision translation stage.

For the flat field system, a flat-field galvonometric scanner was used to scan a focused laser beam from a Nd:YAG laser (1.064 micrometers) across an image plane. A precision translation vacuum stage was located at the image plan and was mounted in a motorized stage so that the material could be translated in the cross-scan direction. The laser power on the film plane was variable from 3–7 watts, and the spot size was about 200 micrometers ($1/e^2$ width). The linear scan speed for the examples cited here was 600 centimeters/second. Microscope glass slides were mounted on the vacuum stage and were used as the receiving substrate. A donor sheet was placed in vacuum contact with the glass and was imaged with the laser by exposure through the polyester side of the donor sheet. The donor and the receptor were translated in a direction perpendicular to the laser scan at a constant velocity. Consequently, colored stripes of equivalent dimensions were transferred to the glass in the imaged areas, since the beam from the laser was not modulated.

For the external drum systems, the material was scanned with a focused laser spot from a collimated/circularized laser diode (SDL, Inc., San Jose, Calif., Model 5422-G1, 811 nanometers). An external drum scanning configuration was utilized. The focused spot size was 8 micrometers (full width at $1/e^2$ level), and the power at the media was 110 milliwatts. The cross-scan translation rate was 4.5 micrometers/drum rotation using a precision translation stage. The circumference of the drum was 84.8 centimeters. The receptor and the donor were attached to the drum using pressure sensitive adhesive tapes. Image data was transferred from a mass-memory system and-supplied to the power supply, which performed the image-wise modulation of the laser diode.

Preparation of Compounds

The materials employed below were obtained from Aldrich Chemical Co. (Milwaukee, Wis.) unless otherwise specified. Melting points (uncorrected) were recorded using a Thomas-Hoover capillary melting point apparatus available from Arthur H. Thomas Co. (Philadelphia, Pa.). NMR spectra were recorded using either a 400 or a 500 MHz Fourier Transform NMR Spectrometer available from Varian Instruments (Palo Alto, Calif.). Infrared spectra were recorded using a Bomem MB102 Fourier Transform IR Spectrometer available from Bomem/Hartmann & Braun (Quebec, Calif.). Molecular weights were determined using an Extrel Fourier Transform Mass Spectrometer from Extrel Corporation (Pittsburgh, Pa.).

For polymer molecular weight determination, gel permeation chromatography (GPC) analyses were recorded on a HP 1090 chromatograph with a HP 1047A refractive index detector available from Hewlett Packard Co. (Palo Alto, Calif.) and Jordi Associates mixed bed pore size and W-100 angstrom columns available from Jordi Associates, Inc. (Bellingham, Mass.). Calibration was based on polystyrene standards from Pressure Chem. Co. (Pittsburgh, Pa.). Samples were prepared in THF (4 mg/mL), filtered through a 0.2 micrometer TEFLON filter, followed by injection of sample (100 microliters).

Compound I: 5-Diazo-2,2-dimethyl-4,6-dioxo-1,3-dioxane

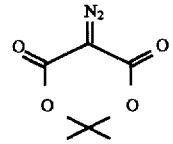

5-Diazo-2,2-dimethyl-4,6-dioxo-1,3-dioxane (often referred to as "Meldrum's Diazo") was purchased from TCI America, Portland, Oreg.

Compound II: 5-Diazo-4,6-diketo-2-methyl-2-(2-phenethyl)-1,3-dioxane.

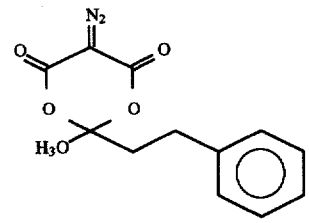

5-Diazo-4,6-dioxo-2-methyl-2-(2-phenethyl)-1,3-dioxane (often referred to as Benzyl Acetone Meldrum's Diazo) was prepared according to the protocol described in Chem. Ber., 94,929 (1961) and Example 1 of U.S. Pat. No. 4,339,522 (Budanson et al.). The precursor 4,6-dioxo-2-methyl-2-(2-phenethyl)-1,3-dioxane was prepared by adding to a 100 mL round bottom flask benzyl acetone (14.8 grams, 0.1 mole), acetic anhydride (10.2 grams, 0.1 mole) and malonic acid (10.4 grams, 0.1 mole). This suspension was warmed gently on a steam bath and 10 mL of ethyl acetate was added to achieve a homogeneous solution. After cooling to room temperature (i.e., 25°–30° C.), 4 drops of concentrated perchloric acid was added and the reaction stirred overnight. The ethyl acetate was removed by rotary evaporation and the residue dissolved with warming in isopropanol (approximately 50 mL). After cooling the solid was isolated by filtration (8.5 grams, 40% yield).

Into a 100 mL round bottom flask was placed p-toluenesulfonyl chloride (2 grams, 10.5 mmol), sodium azide (0.68 gram, 10.5 mmol), and 30 mL of 30:70 (volume-volume) water-ethanol. This solution was stirred at room temperature for 30 minutes. To this solution was added 4,6-dioxo-2-methyl-2-(2-phenethyl)-1,3-dioxane (2.34 grams, 10 mmol) and triethylamaine (1.06 grams, 10.5 mmol). The solution was stirred for 2 hours. The reaction mixture was diluted with water (100 mL) and extracted with petroleum ether (2×100 mL). The organic layer was washed with saturated sodium chloride solution (100 mL), dried over anhydrous magnesium sulfate, and concentrated to give a pale yellow solid. The crude solid was recrystallized from ethanol to give 5-diazo-4,6-dioxo-2-methyl-2-(2-phenethyl)-1,3-dioxane (1.25 grams, 50% yield), m.p. 50°–52° C. The $^1$H NMR and IR spectra were consistent with the proposed product.

Compound III: Diethyl 2-diazomalonate.

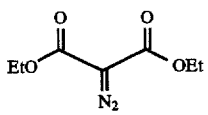

A mixture of sodium azide (683 mg, 10.5 mmol), p-toluenesulfonyl chloride (2.0 grams, 10.5 mmol), and 70% aqueous ethanol (30 mL) was stirred at room temperature for 1 hour. Diethyl malonate (1.62 mL, 10.0 mmol) and triethylamine (1.46 mL, 10.5 mmol) were added. The reaction mixture was stirred at room temperature for 1.5 hours and then poured into deionized water (200 mL). The mixture was extracted with petroleum ether. The extracts were combined and decanted from the solid that formed. The petroleum ether solution was washed with a saturated aqueous sodium chloride solution. The organic solution was dried using anhydrous magnesium sulfate, filtered, and concentrated to give 1.65 grams of diethyl 2-diazomalonate as a yellow oil. IR (KBr): 2138, 1757, 1735, 1320, 1092 cm$^{-1}$. Decomposition temperature: 175° C. (by DSC).

Compound IV: Poly(2-diazo-3-oxobutyroxyethyl methacrylate).

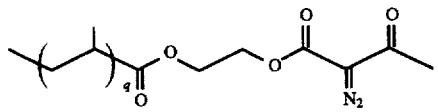

A mixture of 2-diazo-3-oxobutyroxyethyl methacrylate (4.39 grams, 18.3 mmol), toluene (7 mL), hexanethiol (30 mL, available from Eastman Chemical, Kingsport, Tenn.), and 2,2'-azobis(2,4-dimethyl-valeronitrile) (12 mg, available from Polysciences, Inc., Warrington, Pa.) was stirred at 65° C. for 6 hours. The reaction mixture was poured into petroleum ether (100 mL) and allowed to stand overnight. The solvent was decanted from the solidified polymer. The residue was dried under vacuum (<1300 Pascals) at room temperature to give 3.60 grams of poly(2-diazo-3-oxobutyroxyethyl methacrylate) as a pale yellow solid. IR: 2124 cm$^{-1}$. $M_w$=52,000; $M_n$=20,200; q=~84.

Compound V: 2-Diazo-3-oxobutyroxyethyl methacrylate.

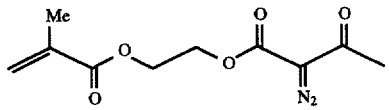

2-Diazo-3-oxobutyroxyethyl methacrylate was prepared according to the protocol described in Y. K. Rao et al., Indian J. Chem., 25B, 735 (1986). A mixture of 2-acetoacetoxyethyl methacrylate (4.28 g, 20 mmol, available from Eastman Chemical, Kingsport, Tenn.), dichloromethane (30 mL), and p-toluenesulfonyl azide (3.94 grams, 20 mmol) was cooled to 0° C. and then DBU (1,8-diazabicyclo[5.4.0]undec-7-ene, 4.48 mL, 30 mmol) was added dropwise. After the addition of DBU, the reaction mixture was stirred at room temperature for 15 minutes and then poured into a mixture of 10% KOH (100 mL) and diethyl ether (50 mL). The organic layer was separated and the aqueous layer was re-extracted with diethyl ether (50 mL). The organic extracts were combined and then washed sequentially with 3N HCl (50 mL), deionized water (2×50 mL) and saturated aqueous sodium chloride solution (50 mL). The organic layer was dried using anhydrous magnesium sulfate, filtered, and concentrated to give 4.39 grams of 2-diazo-3-oxobutyroxyethyl methacrylate as a pale yellow oil. $^1$H NMR (400 MHz, CDCl$_3$): δ 1.94 (s, 3H); 2.47 (s, 3H); 4.35–4.55 (m, 4H); 5.60 (s, 1H); 6.12 (s, 1H). IR: 2181 cm$^{-1}$. Decomposition temperature: 156° C. (by DSC).

Compound VI: Dimedone Diazo.

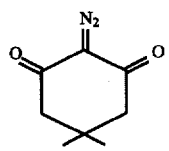

Dimedone Diazo was prepared according to the protocol described in Y. K. Rao et al., Indian J. Chem., 25B, 735 (1986). A mixture of dimedone (2.8 grams, 20 mmol), dichloromethane (30 mL), and p-toluenesulfonyl azide (3.94 grams, 20 mmol) was cooled to 0° C. and then DBU (1,8-diazabicyclo[5.4.0]undec-7-ene, 4.48 g, 30 mmol) was added dropwise. After the addition of DBU, the reaction mixture was stirred at room temperature for 15 minutes and then poured into a solution of 10% KOH (100 mL). The organic layer was separated and washed sequentially with 3N HCl (50 mL), deionized water (2×50 mL), and saturated aqueous sodium chloride solution (50 mL). The organic layer was dried using anhydrous magnesium sulfate, filtered, and concentrated to give an orange solid. The solid was purified by column chromatography on silica gel using petroleum ether/ethyl acetate (65:35) as the eluent to give 2.10 grams dimedone diazo as a pale yellow solid (m.p. 108°–109° C.). $^1$H NMR (400 MHz, CDCl$_3$): δ 1.09 (s, 6H); 2.41 (s, 4H).

Compound VII: 2-Diazo-1-phenyl-1,3-butanedione.

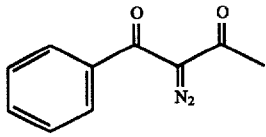

A mixture of sodium azide (683 mg, 10.5 mmol), p-toluenesulfonyl chloride (2.0 grams, 10.5 mmol), and 70% aqueous ethanol (30 mL) was stirred at room temperature for 1 hour. 1-Benzoylacetone (1.62 grains, 10.0 mmol) and triethylamine (1.46 mL, 10.5 mmol) were added. The reaction mixture was stirred at room temperature for 3 hours and then poured into deionized water (200 mL). The mixture was extracted with petroleum ether (2×200 mL). The extracts were combined and then washed with a saturated aqueous sodium chloride solution. The organic solution was dried using anhydrous magnesium sulfate, filtered, and concentrated to give 0.980 grams of 2-diazo-1-phenyl-1,3-butanedione as a yellow oil. Decomposition temperature: 128° C. (by DSC).

Compound VIII: Di-t-butyl-2-diazomalonate.

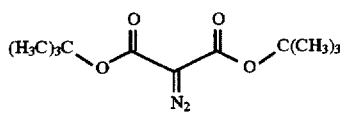

A mixture of sodium azide (1.37 grams, 21.0 mmol), p-toluenesulfonyl chloride (4.0 grams, 21.0 mmol), and 70% aqueous ethanol (60 mL) was stirred at room temperature for 1 hour. Di-t-butyl malonate (4.48 mL, 20.0 mmol) and triethylamine (2.92 grams, 21.0 mmol) were added. The reaction mixture was stirred at room temperature for 4 hours and then poured into deionized water (200 mL). The mixture was extracted with petroleum ether (2×200 mL). The extracts were combined and then washed with a saturated aqueous sodium chloride solution. The organic solution was dried using anhydrous magnesium sulfate, filtered, and concentrated to give 6.10 grams of di-t-butyl-2-diazomalonate as a yellow oil. IR(film): 2110 cm$^{-1}$. Decomposition temperature: 178° C. (by DSC).

Compound IX: Di-t-butyl-2,4-diazo-3-oxo-glutarate (Bis Diazo).

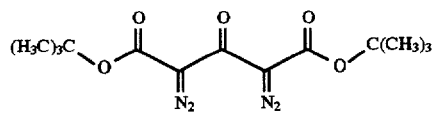

A mixture of sodium azide (930 mg, 14.3 mmol), p-toluenesulfonyl chloride (2.71 grams, 14.3 mmol), and 70% aqueous ethanol (46 mL) was stirred at room temperature for 1 hour. Di-tert-butyl 1,3-acetonedicarboxylate (2.0 grams, 7.74 mmol) and triethylamine (2.27 mL, 16.3 mmol) were added. The reaction mixture was stirred at room temperature for 5 hours and then poured into deionized water (200 mL). The mixture was extracted with petroleum ether (2×150 mL). The extracts were combined and decanted from the solid that formed. The organic solution was washed sequentially with 5% KOH (100 mL) and a saturated aqueous sodium chloride solution. The organic solution was dried using anhydrous magnesium sulfate, filtered, and concentrated to give a yellow oil. The oil was concentrated under high vacuum (<1300 Pascals) to give a pale yellow solid. $^1$H NMR (500 MHz, CDCl$_3$): δ 1.50 (s). $^{13}$C NMR (125.7 MHz, CDCl$_3$): δ 27.83, 28.05, 83.10, 159.76, 175.33.

Compound X: Ethyl-2-diazo-3-oxo-3-phenylpropanate.

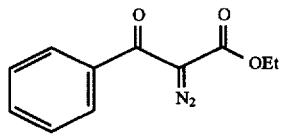

A mixture of sodium azide (1.37 grams, 21.0 mmol), p-toluenesulfonyl chloride (4.0 grams, 21.0 mmol), and 70% aqueous ethanol (60 mL) was stirred at room temperature for 1 hour. Ethyl benzoylacetate (3.50 mL, 20.0 mmol) and triethylamine (2.92 mL, 21.0 mmol) were added. The reaction mixture was stirred at room temperature for 3.5 hours and then poured into deionized water (200 mL). The extracts were combined and decanted from the solid that formed. The organic solution was washed with a saturated aqueous sodium chloride solution. The organic solution was dried using anhydrous magnesium sulfate, filtered, and concentrated to give 3.73 grams of 2-diazo-3-oxo-3-phenylpropanate as a yellow oil. Decomposition temperature: 152° C. (by DSC).

Compound XI: 3-Diazo-1,8,8-trimethylbicyclo[3.2.1]octan-2,4-dione.

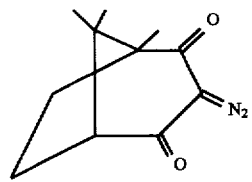

3-Diazo-1,8,8-trimethylbicyclo[3.2.1]octan-2,4-dione (often referred to as methylene camphoroquinone diazo) was prepared according to the protocol described in V. B. Eisert et al., *Liebigs Ann. Chem.*, 659, 64 (1962). A mixture of sodium azide (0.126 grams, 1.94 mmol), p-toluenesulfonyl chloride (0.369 grams, 1.94 mmol), and 70% aqueous ethanol (6 mL) was stirred at room temperature for one hour. 1,8,8-Trimethylbicyclo[3.2.1]octan-2,4-dione (0.332 grams, 1.84 mmol) and triethylamine (0.270 mL, 1.94 mmol) were added. The reaction mixture was stirred at room temperature overnight and then poured into deionized water (50 mL). The mixture was extracted with petroleum ether (2×50 mL). The extracts were combined and washed with a saturated aqueous sodium chloride solution. The organic solution was dried using anhydrous magnesium sulfate, filtered, and concentrated to give a pale yellow solid. The solid was washed with a small amount of cold (5° C.) petroleum ether and dried to give 0.130 gram of 3-diazo-1,8,8-trimethiylbicyclo[3.2.1]octan-2,4-dione as a white solid. $^1$H NMR (400 MHz; CDCl$_3$): δ 1.01 (s, 3H); 1.04 (s, 3H); 1.17 (s, 3H); 1.75–1.83 (m, 1H); 1.90–2.00 (m, 2H); 2.20–2.34 (m, 1H); 2.60 (d, 1H). Decomposition temperature: 145° C. (by DSC).

Examples 1–5 and Comparative Examples 1–2

Examples 1–5 and Comparative Examples 1–2 compare several compounds and polymers for their efficiency in thermal mass transfer from a donor to a receptor using the internal drum system. These examples illustrate that the efficiency of laser-induced thermal mass transfer depends on many factors, including the decomposition temperature of energetic materials, the exothermicity of the decomposition, the ability to generate pressure by gas production either through decomposition or vaporization, and the temperature dependence of vaporization.

A series of coating solutions were prepared, with each solution containing 0.25 gram of 20% by weight novolac resin SD-126A (Borden Packaging & Industrial Products, Louisville, Ky.) in MEK, 0.05 gram IR-165 near infrared dye (Glendale Protective Technologies, Lakeland, Fla.) having the structure

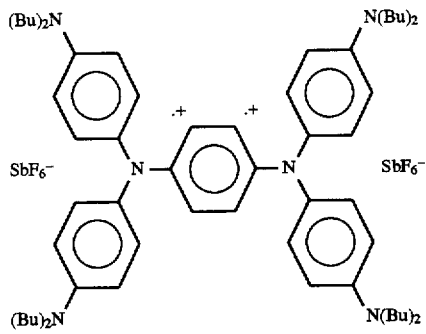

and 0.015 gram of Indolenine Red magenta dye (Color Index 48070) as its perfluoro-4-ethylcyclohexane sulfonate salt (IR PECHS), having the following structure

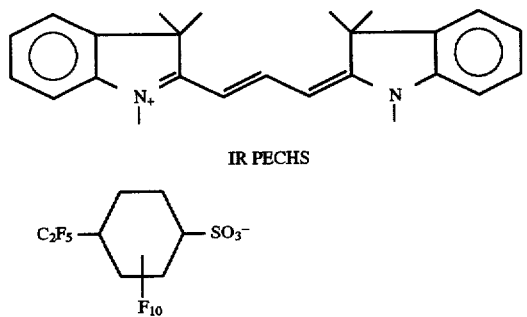

which is prepared by the metathesis reaction between Indolenine Red chloride and potassium perfluoro-4-ethylcyclohexane sulfonate in water as taught in U.S. Pat. No. 4,307,182 (Dalzell et al.); and used to help visualize the coating and transferred image), 0.7 gram methylethylketone (MEK), and 0.05 gram of one of the following diazo compounds, diazo compound precursors, or vaporizable solids: Example 1 included Compound I (Meldrum's Diazo); Example 2 included Compound II (Benzyl Acetone Meldrum's Diazo); Example 3 included Compound VI (Dimedone Diazo); Example 4 included Compound IX (Bis Diazo); Example 5 included Compound XI (Methylene Camphoroquinone Diazo); Comparative Example 1 included methylene camphoroquinone, which has the structure:

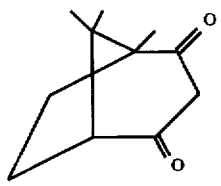

and Comparative Example 2 included camphor.

Each of Examples 1–5 and Comparative Examples 1 and 2 were coated onto 58 micrometer thick polyester using a No. 4 coating rod (RD Specialties, Webster, N.Y.) and dried 2 minutes at 80° C. to give nontacky, transparent donor films. The donor films were contacted to 150 micrometer thick grained, anodized, and silicated aluminum printing plate receptors under vacuum in the internal drum exposure unit. These donor/receptor samples were then exposed through the polyester side of the donor sheets. After peeling the exposed donor sheet off the receptor, the width of the transferred lines on the receptor were measured in micrometers, and the threshold energy for thermal mass transfer was calculated. The results are listed in Table 1 below.

Example 6

A solution consisting of 0.055 gram diazo polymer Compound IV, 0.07 gram IR-165 dye, 0.015 gram IR PECHS dye and 0.9 gram MEK was coated with a No. 4 coating rod onto 58 micrometer thick polyester and dried. The resulting donor was exposed as in Examples 1–5 using the internal drum system. The results are recorded in Table 1 below.

Comparative Example 3

A solution consisting of 0.055 gram of the same polymer used in Example 6 but without the diazo groups and having the following structure (wherein the number of repeating units "r" can be about 70–100):

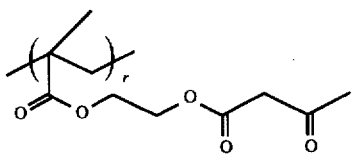

in combination with 0.03 gram IR-165 dye, 0.007 gram IR PECHS dye, and 0.453 gram MEK was coated onto 58 micrometer thick polyester with a No. 4 coating rod and dried. The resulting donor was exposed as in Examples 1–5. The results are recorded in Table 1 below.

Comparative Example 4

A solution consisting of 0.5 gram of 20% by weight novolac resin SD-126A in MEK, 0.05 gram IR-165 dye, 0.015 gram IR PECHS dye and 0.5 gram MEK was coated onto 58 micrometer thick polyester with a No. 4 coating rod and dried. The resulting donor was exposed as in Examples 1–5. The results are recorded in Table 1 below.

Comparative Example 5

A solution consisting of 0.1 gram nitrocellulose (Hercules, Inc., Wilmington, Del.), 0.07 gram IR-165 dye, 0.015 gram IR PECHS dye and 0.9 gram MEK was coated onto 58 micrometer thick polyester with a No. 4 coating rod and dried. The resulting donor was exposed as in Examples 1–5. The results are recorded in Table 1 below.

Comparative Example 6

Diazonium salt perfluorobutane sulfonate resin was prepared by the following metathesis reaction. A solution of 1.13 grams of the potassium salt of perfluorobutanesulfonic acid in 20 grams water and 12.5 grams methanol was added all at once to a solution of 1 gram of the zinc chloride double salt of the condensation product of 4-diazonium diphenylamine with formaldehyde (Minnesota Mining and Manufacturing Co., St. Paul, Minn.) in 20 grams water and 12.5 grams methanol. A precipitate formed immediately which was filtered, washed with 100 milliliters deionized water, and dried to give 1.5 grams of the following resin (wherein "t" is about 2–9):

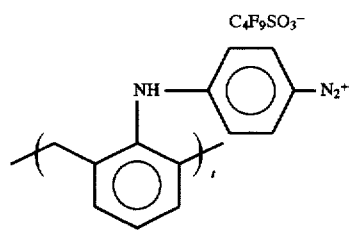

A sample of 0.1 gram of this resin was combined with 0.07 gram IR-165 dye, 0.015 gram IR PECHS dye and 0.9 gram MEK, and was coated onto 58 micrometer thick polyester with a No. 4 coating rod and dried. The resulting donor was exposed as in Examples 1–5. The results are recorded in Table 1 below.

Comparative Example 7

A solution consisting of 0.25 gram of 20% by weight novolac resin SD-126A in MEK and 0.05 gram diazonium salt of the formula

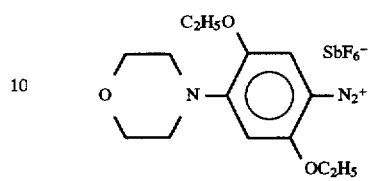

(Esco Co., Ltd. Partnership, Muskegon, Mich.) was combined with 0.07 gram IR-165 dye, 0.015 gram IR PECHS dye and 0.7 gram MEK. The solution was coated onto 58 micrometer thick polyester with a No. 4 coating rod and dried. The resulting donor was exposed as in Examples 1–5. The results are recorded in Table 1 below.

TABLE 1

| Example (E) or Comparative Example (CE) | Compound | TGA Temperature for 5% weight loss | DSC Peak Decomposition Temperature | DSC Exothermic Decomposition Energy | Line Width (micrometers) | Relative Sensitivity (J/cm$^2$) | Relative Sensitivity[1] | Sensitivity[2] |
|---|---|---|---|---|---|---|---|---|
| E-1 | Compound I | 99° C. | 243° C. | 1,118 J/g | 19.8 | 0.039 | 2.5 | 1.2 |
| E-2 | Compound II | 163° C. | 246° C. | 870 J/g | 17.6 | 0.049 | 2.0 | 0.96 |
| E-3 | Compound VI | 93° C. | 149° C. | 1,180 J/g | 35.3 | 0.003 | 32.7 | 15.7 |
| E-4 | Compound IX | 104° C. | 152° C. | 810 J/g | 22.0 | 0.029 | 3.4 | 1.6 |
| E-5 | Compound XI | 102° C. | 145° C. | 740 J/g | 26.1 | 0.016 | 6.1 | 2.9 |
| CE-1 | Methylene camphoroquinone | 93° C. | — | — | 19.0 | 0.042 | 2.3 | 1.1 |
| CE-2 | Camphor | 59° C. | — | — | 19.4 | 0.040 | 2.5 | 1.2 |
| E-6 | Compound IV | 143° C. | 165°0 C. | 700 J/g | 20.0 | 0.038 | 2.6 | 1.2 |
| CE-3 | (structure) | — | — | — | <5 | >0.11 | <0.89 | <0.42 |
| CE-4 | Novalac resin | 261° C. | — | — | 18.1[3] | 0.047 | 2.1 | 1 |
| CE-5 | Nitrocellulose | — | 215° C. | 3,730 J/g | 8.7 | 0.098 | 1 | 0.48 |
| CE-6 | (structure) | — | 144° C. | 490 J/g | 14.0 | 0.069 | 1.42 | 0.68 |
| CE-7 | (structure) | — | 139° C. | 580 J/g | 18.7 | 0.044 | 2.2 | 1.1 |

[1]Sensitivity relative to that for nitrocellulose.
[2]Sensitivity relative to that for novalac resin.
[3]This is an average of 8–10 samples.

Several observations can be drawn from the results presented in Table 1 for Examples 1–6 and Comparative Examples 1–7. Comparative energetic materials nitrocellulose (CE-5), diazonium salt resins (CE-6), and diazonium salts (CE-7), which have been purported to be useful in thermal mass transfer systems, do not perform as well from a sensitivity standpoint as the diazo polymer Compound IV (E-6), novolac resin containing various diazo compounds I, II, VI, IX, and XI (E-1–5), and certain vaporizable solids such as methylene camphoroquinone and camphor (CE-1 and CE-2). Although Compounds I, II, and VI are very similar in structures, they give profoundly different sensitivities. This may be due to the fact that Compound II has a high vaporization temperature and a high decomposition temperature, thereby having low sensitivity. Compound I has a much lower vaporization temperature but nearly the same decomposition temperature as Compound II, and therefore has intermediate sensitivity. Compound VI has both a low vaporization temperature and a low decomposition temperature, thereby resulting in high sensitivity. Therefore, an increase in sensitivity can be achieved by use of materials with either a low vaporization temperature (e.g., compounds such as camphor and methylene camphoroquinone give good sensitivities, yet do not decompose energetically) or a low exothermic decomposition temperature. Note in the examples that compounds with an exothermic decomposition temperature above 200° C. and a high vaporization temperature result in low sensitivities under the conditions of these experiments (e.g., nitrocellulose and Compound II). Compound VI has exceptionally high sensitivity, possibly as a result of low vaporization and decomposition temperatures in combination with a highly exothermic decomposition, conditions which are implied by TGA and DSC results.

Examples 7–9 and Comparative Examples 8–10

Coating solutions were prepared consisting of 0.5 gram of 10% by weight of the polymers listed in Table 2 in MEK, from 0 gram to 0.05 gram Compound I, 0.05 gram IR-165 dye, 0.015 gram IR PECHS dye and 0.45 gram MEK. These solutions were coated onto 58 micrometer thick polyester, dried and exposed as in Example 1. Table 2 below lists the line widths of ablated mass transfer material on the aluminum receptor.

TABLE 2

| Example (E) or Comparative Example (CE) | Polymer | Compound I (grams) | Line width (micrometers) |
| --- | --- | --- | --- |
| E-7 | Butvar B76[1] (Polyvinylbutyral) | 0.05 | 9.4 |
| CE-8 | Butvar B76 | 0 | 6.4 |
| E-8 | Saran F310[2] (polyvinylidene chloride) | 0.05 | 11.9 |
| CE-9 | Saran F310 | 0 | 6.9 |
| E-9 | Cellulose Acetate Butyrate 551-0.01[3] | 0.05 | 17.6 |
| CE-10 | Cellulose Acetate Butyrate 551-0.01 | 0 | 9.92 |

[1]Monsanto Co. St. Louis, MO
[2]Dow Chemical Co., Midland, MI
[3]Eastman Chemical Co., Kingston, TN The coatings containing Compound I gave higher line widths (greater sensitivities) for all the polymers tested.

Example 10

Near Infrared Dye I was prepared by the following procedure. Q SWITCH V perchlorate (Eastman Laboratory Chemicals, Rochester, N.Y.) (0.1 gram) and $(CF_3SO_2)_3C^- Cs^+$ (0.07 gram) were added to MEK (100 mL) in a 250 mL separatory funnel. The mixture was shaken until everything dissolved. Ether (20 mL) was added to the MEK solution to increase its incompatibility with water. The MEK/ether layer was washed sequentially with deionized water (100 mL) and saturated sodium chloride (100 mL), dried over anhydrous magnesium sulfate, and evaporated to dryness on a rotary evaporator to give 0.16 gram of Dye I of the following structure:

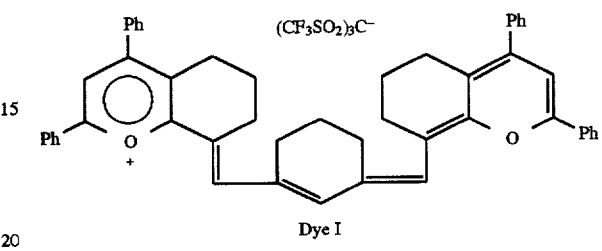

Dye I

A solution containing 0.25 gram of 20% by weight novolac resin SD-126A in MEK, 0.07 gram Dye I, 0.015 gram IR PECHS dye, 0.05 gram Compound I and 0.7 gram MEK was coated onto 58 micrometer thick polyester and dried. The sample was exposed as in Examples 1–5. This donor produced a line width of 15.4 micrometers on the aluminum receptor. When Compound I was left out of the coating, a line width of 14.1 micrometers was obtained, demonstrating that Compound I enhanced the sensitivity of this donor composition.

Example 11

A solution of 0.125 gram of 20% by weight novolac SD-126A in MEK, 0.05 gram IR-165 dye, 0.075 gram Compound I and 0.8 gram MEK was coated with a No. 4 coating rod onto 58 micrometer thick polyester film and dried for 2 minutes at 80° C. This coating was then topcoated with "SCOTCHPRINT" Magenta Toner (Minnesota Mining and Manufacturing Co., St. Paul, Minn.) with a No. 4 coating rod and dried for 2 minutes at 80° C. The resulting donor was put in contact with plain copy paper under vacuum in the exposure device described in Examples 1–5. The magenta toner readily transferred to plain paper at scan speeds of 160 meters/second and 192 meters/second. When Compound I was left out of the bottom layer, poor transfer occurred at both scan speeds. This example demonstrates the use of a diazo compound in a two-layer system to enhance sensitivity.

Example 12

A dispersion consisting of 0.17 gram of 20% by weight novolac resin SD-126A in MFK, 0.2 gram of a 23% by weight millbase dispersion in MEK consisting of a 3:2 ratio of cyan pigment and VAGH binder (vinyl chlofide-acetate, Union Carbide Chemicals and Plastics, Inc., Danbury, Conn.), 0.05 gram Compound I 0.05 gram IR-165 dye and 0.61 gram MEK was coated onto 58 micrometer thick polyester film with a No. 4 coating rod and dried for 2 minutes at 80° C. This donor was then imaged against a smooth paper receptor (7600 paper, Minnesota Minimig and Manufacturing Co., St. Paul, Minn.) as in Example 11. A cyan line with width of 22 micrometers was achieved on the paper after exposure at a scan speed of 160 meters/second. When Compound I was left out of the donor layer, poor transfer occurred to the smooth paper at the same scan speed. This example demonstrates the use of a diazo compound to enhance the sensitivity of thermal transfer of a donor layer containing colored pigment.

Example 13

A solution consisting of 0.3 gram Compound IV, 0.05 gram IR-165 dye, 0.015 gram IR PECHS dye and 2.7 gram MEK was coated onto 58 micrometer thick polyester using a No. 4 coating bar and dried for 2 minutes at 80° C. A halftone scale (1-100% dots, 1% increments, 175 line screen) was transferred from the donor to aluminum receptor according to the exposure conditions in Examples 1-5. Analysis of the receptor showed that 1-99% dots had been transferred to the aluminum. A halftone magenta color separation of an image was also transferred in the same manner. The resulting plate was baked for two minutes at 180° C. and ran on a Heidelberg GTO press with black lithographers ink for 1000 copies with no evidence of image wear on the plate.

Example 14

A solution consisting of 0.3 gram of 20% by weight Borden novolac resin SD-126A in MEK, 0.4 gram of 5% by weight Resimene 747 (melamine formaldehyde resin, Monsanto Co., St. Louis, Mo.) in MEK, 0.02 gram Compound VI, 0.05 gram IR-165 dye, 0.015 gram IR PECHS dye and 0.28 gram MEK was coated onto 58 micrometer thick polyester film with a No. 4 coating rod and dried 2 minutes at 80° C. A halftone scale (1-100%, 175 line) and a halftone image were transferred from the donor to the aluminum at a scan speed of 160 meters/second according to the exposure conditions in Example 1-5. 1-99% dots were transferred to the aluminum in the halftone scale. The plate was baked for 1 minute at 384° C. and was run for 1000 copies on a Heidelberg GTO printing press using black lithographers ink with no evidence of image wear on the plate.

Example 15

A solution consisting of 0.22 gram of 20% by weight Borden novolac resin SD-126A in MEK, 0.08 gram of 20% by weight of an acrylated epoxy (Ebecryl 3605) bisphenol-A base (UCB Radcure, Inc., Livingston, N.J.) in MEK, 0.04 gram Compound VI, 0.04 gram IR-165 dye, 0.015 gram IR PECHS dye and 0.66 gram MEK was coated onto 58 micrometer thick polyester film with a No. 4 coating rod and dried 2 minutes at 80° C. A halftone scale (1-100%, 175 line) and a halftone image were transferred from the donor to the aluminum at a scan speed of 160 meters/second according to the exposure conditions in Example 1. Dots (1-99%) were transferred to the aluminum in the halftone scale. The plate was baked for 1 minute at 384° C. and was run for 1000 copies on a Heidelberg GTO printing press using black lithographers ink with no evidence of image wear on the plate.

Example 16

A solution consisting of 0.085 gram Compound IV, 0.015 gram Compound VI, 0.05 gram IR-165 dye, 0.015 gram IR PECHS dye and 0.9 gram MEK was coated onto 58 micrometer thick polyester using a No. 4 coating bar and dried for 2 minutes at 80° C. The donor was placed in face-to-face contact with copper plated Kapton receptor (E. I. DuPont de Nemours, Wilmington, Del.). This assembly was imaged with the device used in Examples 1-5 at a scan speed of 160 meters/second to create circuit and line patterns. Lines of 30 micrometer width and 42 micrometer pitch were demonstrated to be feasible with this method. Coating transferred from the donor to the receptor to provide an etch resist on the surface of the copper. The image was baked for 2 minutes at 180° C., and the metal surface was patterned by etching the exposed copper with a solution consisting of 50 mL concentrated sulfuric acid, 400 mL water and 50 mL of 30% aqueous hydrogen peroxide for approximately three minutes at room temperature to completely remove the metal, leaving only the Kapton polymer in the areas that did not receive the resist. The resist was removed by wiping with a cotton swab soaked in MEK. The result of the process is a copper circuit on a Kapton substrate. Poor transfer resulted when Compound VI was left out of the donor coating.

Example 17

A 23% by weight cyan pigment millbase was prepared in methylethyl ketone consisting of 47.17 gram cyan pigment 248-0165 (Sun Chemical Corp., Fort Lee, N.J.), 47.17 gram VAGH resin (Union Carbide Chemicals and Plastics Co., Inc., Danbury, Conn.), 5.66 gram Disperbyk 161 (BYK Chemie, Wallingford, Conn.) and 335 gram MEK. A dispersion consisting of 0.5 gram of the cyan pigment millbase, 0.05 gram IR-165 dye, 0.02 gram diazo Compound VI and 0.6 gram MEK was coated with a No. 4 coating rod onto 58 micrometer thick polyester. The donor was contacted to a microscope glass slide receptor and put in the flat field scanner system. The donor/receptor combination was exposed through the polyester side of the donor at 3.5 watts and 7 watts to transfer lines of cyan pigment coating from the donor to the glass receptor with a width of approximately 117 micrometers and approximately 164 micrometers, respectively.

Example 18

A solution consisting of 0.1 gram of 20% by weight novolac resin SD-126A in MEK, 0.08 gram Compound VI, 0.05 gram IR-165 dye and 0.82 gram MEK was coated with a No. 4 coating rod onto 58 micrometer thick polyester film and dried for 2 minutes at 80° C. A mixture consisting of 0.25 gram of an Aquis II phthalo green GW-3450 pigment dispersion (Heucotech, Ltd., Fairless Hills, Pa.), 0.75 gram water and 3 drops of 5% by weight FC-170 surfactant (Minnesota Mining and Manufacturing Co., St. Paul, Minn.) in water was then coated on top of the first layer using a No. 4 coating rod and dried for 2 minutes at 80° C. This donor was exposed in contact with a microscope glass slide receptor as in Example 17 at 5 watts to give lines of transferred green pigment layer approximately 140 micrometers wide on the receptor. The lines were somewhat jagged and contained many pinholes. The Example was repeated by substituting Aquis II QA magenta RW-3116 pigment dispersion (Heucotech, Ltd., Fairless Hills, Pa.) and Aquis II phthalo blue G/BW-3570 pigment dispersion (Heucotech, Ltd., Fairless Hills, Pa.) for Aquis II phthalo green GW-3450 pigment dispersion to give similar results. Very little transfer occurred under these exposure conditions if Compound VI was left out of the bottom layer.

Example 19

Example 18 was repeated except that 3 drops of Joncryl 74 (acrylic resin solution, S.C. Johnson and Son, Inc., Racine, Wis.) were added to the mixture containing the Aquis II QA magenta RW-3116 pigment dispersion before coating. Exposure as in Example 18 at 5 watt produced lines of approximately 160 micrometers on the glass receptor with little or no pinholes.

Example 20

A solution consisting of 0.1 gram Compound IV, 0.05 gram IR-165 dye, 0.015 gram IR PECHS dye and 0.9 gram MEK was coated with a No. 4 coating rod onto 58 micrometer thick polyester and dried for 2 minutes at 80° C. This donor sheet was contacted to a microscope glass slide receptor and exposed according to Example 17 to give transferred lines on the glass receptor of approximately 175 micrometers and 135 micrometers at 7 watts and 3.5 watts, respectively.

Example 21

A solution consisting of 0.5 gram of 10% by weight novolac resin SD-126A in MEK, 0.05 gram Compound VI, 0.03 gram of the near infrared dye of the following structure (prepared according to the procedure of U.S. Pat. No. 5,360,694 (Thien et al.):

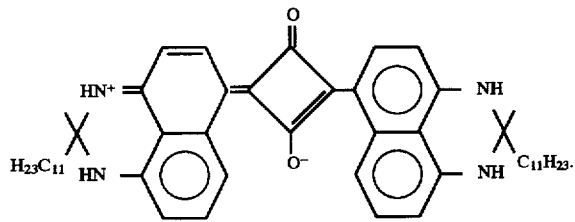

along with 0.015 gram IR PECHS dye and 0.045 gram MEK was coated with a No. 4 coating bar onto 58 micrometer thick polyester film and dried for 2 minutes at 80° C. The donor film was contacted to a 150 micrometer grained, anodized, and silicated aluminum printing plate receptor in the external drum exposure unit. These donor/receptor samples were then exposed through the polyester side of the donor sheets using the unmodulated laser diode. Excellent transfer of material occurred from the donor to the aluminum receptor at drum speeds from 170 centimeters/second to 933 centimeters/second.

Comparative Example 11

Example 21 was repeated, except that Compound VI was left out of the donor sheet coating. The donor without Compound VI gave transfer to the aluminum receptor at drum speeds of up to 678 centimeters/second comparable to the donor of Example 21. However the donor sheet without Compound VI gave inferior transfer to the aluminum receptor at drum speeds of 763 centimeters/second and 933 centimeters/second compared to the donor sheet of Example 21. These results indicate that Compound VI results in improved transfer of novolac resin from a polyester donor sheet to an aluminum printing plate receptor when using the external drum scanner and a laser diode source at 811 nm.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A diazo compound of the formula:

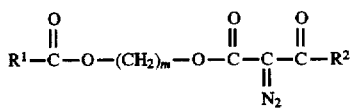

wherein $R^1$ is H, a $(C_1-C_4)$aliphatic group, or

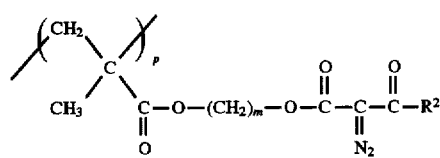

wherein $p=2-1000$; $R^2$ is H or an organic group; and $m=2-10$.

2. The diazo compound of claim 1 wherein $R^1$ is a $(C_2-C_4)$alkenyl group.

* * * * *